United States Patent
Almås et al.

(10) Patent No.: US 9,492,479 B2
(45) Date of Patent: Nov. 15, 2016

(54) COMPOSITIONS OF HYPOCHLOROUS ACID (HOCl) AND METHODS OF MANUFACTURE THEREOF

(71) Applicant: WIAB WATER INNOVATION AB, Malmo (SE)

(72) Inventors: Geir Hermod Almås, Oslo (NO); Adrian Bignami, Malmo (SE)

(73) Assignee: Wiab Water Innovation AB, Malmo (SE)

( * ) Notice: Subject to any disclaimer, the term of this patent is extended or adjusted under 35 U.S.C. 154(b) by 849 days.

(21) Appl. No.: 13/770,738

(22) Filed: Feb. 19, 2013

(65) Prior Publication Data

US 2013/0216628 A1    Aug. 22, 2013

Related U.S. Application Data

(60) Provisional application No. 61/600,344, filed on Feb. 17, 2012.

(51) Int. Cl.
*A61K 33/20* (2006.01)
*C01B 11/04* (2006.01)
*A61K 31/19* (2006.01)

(52) U.S. Cl.
CPC .............. *A61K 33/20* (2013.01); *A61K 31/19* (2013.01); *C01B 11/04* (2013.01)

(58) Field of Classification Search
USPC .......................................... 424/600; 423/473
See application file for complete search history.

(56) References Cited

U.S. PATENT DOCUMENTS

| | | | |
|---|---|---|---|
| 5,152,915 A | 10/1992 | Ralston, Jr. et al. | |
| 6,564,508 B1 * | 5/2003 | Buchan | A01G 7/00 47/1.5 |
| 8,784,900 B2 * | 7/2014 | Northey | A61K 33/20 252/181.4 |
| 2009/0258083 A1 * | 10/2009 | Calderon | C01B 11/04 424/600 |

FOREIGN PATENT DOCUMENTS

| | | |
|---|---|---|
| JP | 2007-326050 A | 12/2007 |
| JP | 2011-229833 A | 11/2011 |
| WO | 94/21125 A1 | 9/1994 |

OTHER PUBLICATIONS

International Search Report and Written Opinion mailed Jul. 30, 2013, for International Application No. PCT/IB2013/000682, filed Feb. 19, 2013 (7 pages).

* cited by examiner

*Primary Examiner* — Michael G Hartley
*Assistant Examiner* — Robert Cabral
(74) *Attorney, Agent, or Firm* — Thomas C. Meyers; Brown Rudnick LLP

(57) ABSTRACT

The invention generally relates to compositions of hypochlorous acid (HOCl) and methods of manufacture thereof. In certain aspects, the invention provides air-free compositions of HOCl. In other aspects, the invention provides methods of making HOCl that involve mixing together in water in an air-free environment, a compound that generates a proton ($H^+$) in water and a compound that generates a hypochlorite anion ($OCl^-$) in water to thereby produce air-free hypochlorous acid.

21 Claims, 7 Drawing Sheets

COMPOSITIONS OF HYPOCHLOROUS ACID (HOCl) AND METHODS OF MANUFACTURE THEREOF

RELATED APPLICATION

The present application claims priority to and the benefit of U.S. provisional application Ser. No. 61/600,344, filed Feb. 17, 2012, the content of which is incorporated by reference herein in its entirety.

FIELD OF THE INVENTION

The invention generally relates to compositions of hypochlorous acid (HOCl) and methods of manufacture thereof.

BACKGROUND

Hypochlorous acid (HOCl) is a weak acid that is known to rapidly inactivate bacteria, algae, fungus, and other organics, making it an effective agent across a broad range of microorganisms. Additionally, since hypochlorous acid is a weak acid and since people naturally produce certain compounds that allow them to tolerate hypochlorous acid (e.g., the amino acid taurin), it is generally not harmful to people. Due to the combination of its biocide properties and its safety profile, hypochlorous acid has been found to have many beneficial uses across many different industries, such as the medical, foodservice, food retail, agricultural, wound care, laboratory, hospitality, dental, or floral industries.

Hypochlorous acid is formed when chlorine dissolves in water. One manufacturing method involves the electrochemical activation of a saturated salt solution (e.g., brine) to form HOCl. Another production method involves the disproportionation of chlorine gas in alkaline solutions.

A problem with hypochlorous acid produced by these methods is that it is highly unstable, and over a short period of time (e.g., a few hours to a couple of weeks) the hypochlorous acid will degrade. The distribution of chloric compounds in aqueous solution is known to be a function of pH. As the pH of a solution containing hypochlorous acid becomes more acidic (e.g., pH below 3), chlorine gas is formed. As the pH of a solution containing hypochlorous acid becomes more basic (e.g., pH above 8) hypochlorite anions (OCl—; i.e., bleach) are formed, which are also toxic to people. Thus, while being an effective biocide, the use of hypochlorous acid has been limited by the need for onsite generation and the challenge of maintaining storage stability.

SUMMARY

The invention recognizes that aspects of the production process for making hypochlorous acid (HOCl) may contribute to the instability of the product. Particularly acidic pH, due to donation of a proton from an acid in the reaction, causes instability in the HOCl composition. Additionally, exposure to air during the production process has been shown to destabilize the HOCl, which destabilization process can escalate quickly. Methods of the invention provide air-free mixing methods for producing hypochlorous acid that do not rely on electrolysis or use of chlorine gas. Methods of the invention produce an air-free, stable formulation of hypochlorous acid that can be bottled and stored for a significant period of time (e.g., from at least a couple of months to 6 to 12 months or longer), eliminating the need for onsite generation and overcoming the challenges of maintaining storage stability.

In certain aspects, methods of the invention involve mixing together in water in an air-free environment, a compound that generates a proton ($H^+$) in water and a compound that generates a hypochlorite anion ($OCl^-$) in water to thereby produce air-free hypochlorous acid. Any compound that produces a hypochlorite anion ($OCl^-$) in water may be used with methods of the invention. Exemplary compounds include NaOCl, $Ca(OCl)_2$, and $Mg(OCl)_2$. In particular embodiments, the compound is NaOCl. Any compound that produces a proton ($H^+$) in water may be used with methods of the invention. Preferred compounds are acids, such as acetic acid ($CH_3CO_2H$), HCl and $H_2SO_4$. Methods of the invention result in the production of a highly-pure and stable HOCl composition with mild buffering capacity (e.g., pH 3.6-5.6 for acetic acid and 6.5-8.5 for HCl). Stability is increased at the lower pH, so low pH buffers are preferred.

Methods of the invention include introducing to water a compound that generates a proton and a compound that generates a hypochlorite anion in any order (e.g., simultaneously or sequentially) and in any manner (aqueous form, solid form, etc.). For example, the compound that generates a proton and the compound that generates the hypochlorite anion are each aqueous solutions and are introduced to the water sequentially, e.g., the compound that generates the proton may be introduced to the water first and the compound that generates the hypochlorite anion may be introduced to the water second. However, methods of the invention include other orders for sequential introduction of the compound that generates the proton and the compound that generates the hypochlorite anion.

Methods of the invention may be conducted with most types of water, including tap water. In certain embodiments, the water is filtered or purified water, such as that obtained from any water purification company, such as Millipore (Billerica, Mass.). In certain embodiments, the water has a buffering capacity from about pH 6 to about pH 8. In certain embodiments, the water has a buffering capacity from about pH 3.6 to about pH 6, but in any case not low enough to produce $Cl_2$ gases. In other embodiments, the water is deionized water to which at least one buffering agent has been added, such as acetic buffer or phosphate buffer. In particular embodiments, an initial pH of the water prior to addition of the acetic acid, HCl or the compound that generates the hypochlorite anion is at least about 8, (e.g., 8.1 or greater, 8.2 or greater, 8.3 or greater, 8.4 or greater, 8.5 or greater, 8.6 or greater, 8.7 or greater, 8.8 or greater, 8.9 or greater, 9.0 or greater, 9.5 or greater, 10.0 or greater, 10.5 or greater, or 10.8 or greater). In specific embodiments, the pH of the water prior to addition of either the compound that generates the proton or the compound that generates the hypochlorite anion is 8.4. In certain embodiments, NaOH is introduced at the beginning of the process to enhance the buffering properties of the final solution.

Generally, the reagents are added to the water in relatively small amounts compared to the flow of water. In certain embodiments, no more than about 0.6 mL amount of the compound that generates the proton is introduced to the water at a single point in time. In other embodiments, no more than about 0.6 mL amount of the compound that generates the hypochlorite anion is introduced to the water at a single point in time.

Generally, the added reagents are turbulently mixed. Such turbulent mixing may be accomplished by using a mixing device that is configured to produce a plurality of vortexes within a mixing chamber. In certain embodiments, the compound that generates the proton is introduced to the water and turbulently mixed with the water prior to the introduction to the water of the compound that generates the hypochlorite anion. Then, the compound that generates the hypochlorite anion is introduced to the water after the compound that generates the proton has been turbulently mixed with the water, and after introduction, the compound that generates the hypochlorite anion is turbulently mixed with the water.

Methods of the invention can be conducted in any type of vessel or chamber or fluidic system. For example, a fluidic system including pipes and mixing devices is used to conduct methods of the invention. In such embodiments, the water is flowing through a pipe, and the reagents (e.g., the compound that generates the proton and the compound that generates the hypochlorite anion) are introduced to the water as it is flowing through the pipe. The mixing devices are in-line with the piping system. Generally, the water in the pipe is flowing at a rate from about 0.1 liters per second to about 1 liter per second and is under a pressure of at least about 0.1 bar, such as for example 1 bar or greater. In certain embodiments, the method is performed under pressure. In certain embodiments, the method is performed in an air-free environment and under pressure. Methods of the invention may be performed manually or in an automated fashion.

Another aspect of the invention provides methods that involve mixing together in water, a compound that generates a proton ($H^+$) and a compound that generates a hypochlorite anion ($OCl^-$) in water to thereby produce hypochlorous acid, in which the method is performed without use of chlorine gas or use of electrolysis.

Another aspect of the invention provides methods that involve turbulently mixing together in water, a compound that generates a proton ($H^+$) and a compound that generates a hypochlorite anion ($OCl^-$) in water to thereby produce hypochlorous acid.

Another aspect of the invention provides methods that involve introducing hydrochloric acid (HCl) to a flow of water having a pH from about 8 to about 9, turbulently mixing the HCl with the flowing water in a first mixing device, introducing sodium hypochlorite (NaOCl) to the water after the water has exited the first mixing device, and turbulently mixing the NaOCl with the flowing water in a second mixing device, thereby producing hypochlorous acid (HOCl), in which the method is performed in an air-free environment and under pressure.

Methods of the invention produce an air-free composition of hypochlorous acid (HOCl). In certain embodiments, the composition is substantially free of chlorine gas. The composition may have a pH from about 4 to about 7.5, more particularly, from about 6.0 to about 7.0. The HOCl may have a concentration of at least about 200 ppm. Compositions of the invention are stable and storable for long periods of time, e.g., from about 1 month to about 1 year.

DETAILED DESCRIPTION

Figure 1:
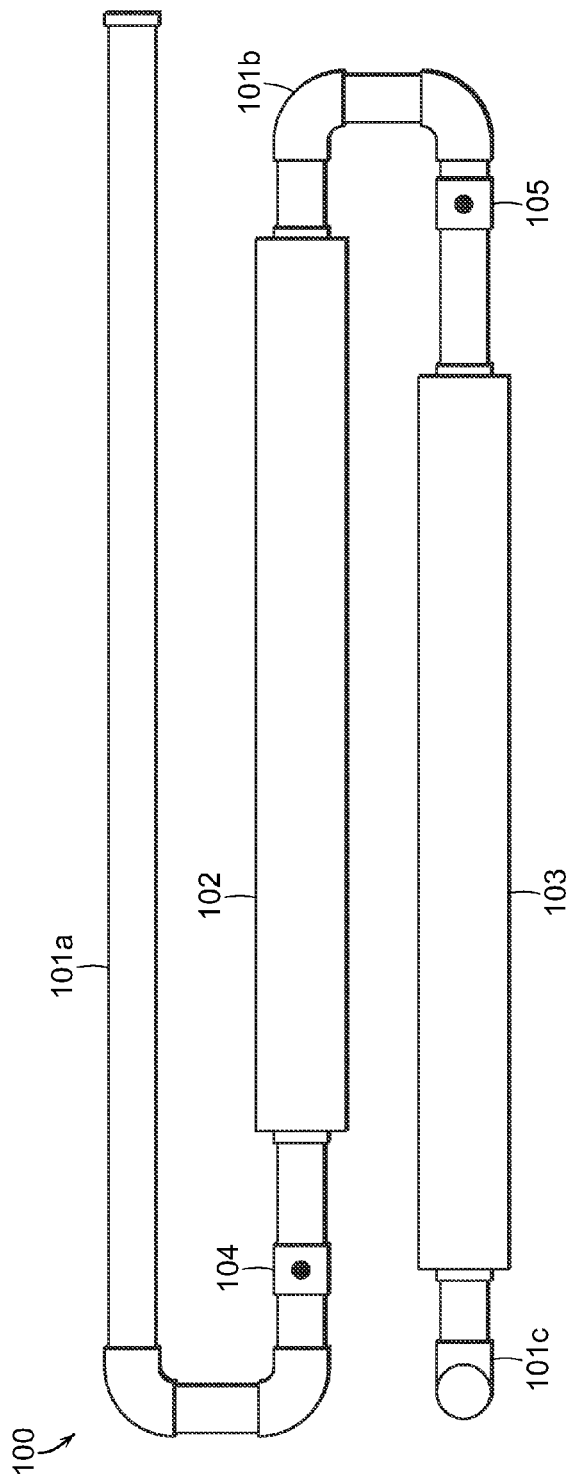
FIG. 1 is a schematic showing an exemplary system for producing hypochlorous acid according to methods of the invention.

The basis of compositions and methods of the invention is the protonation of the hypochlorite ion ($OCl^-$). Using HCl and NaOCl as an example, the protonation is accomplished by introducing an acid (e.g., HCl) to the solution, which results in the following reaction occurring:

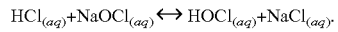

$$HCl_{(aq)} + NaOCl_{(aq)} \longleftrightarrow HOCl_{(aq)} + NaCl_{(aq)}.$$

The hypochlorous acid in aqueous solution partially dissociates into the anion hypochlorite ($OCl^-$), thus in aqueous solution there is always an equilibrium between the hypochlorous acid and the anion ($OCl^-$). This equilibrium is pH dependent and at higher pH the anion dominates. In aqueous solution, hypochlorous acid, is also in equilibrium with other chlorine species, in particular chlorine gas, $Cl_2$, and various chlorine oxides. At acidic pH, chlorine gases become increasingly dominant while at neutral pH the different equilibria result in a solution dominated by hypochlorous acid. Thus, it is important to control exposure to air and pH in the production of hypochlorous acid.

Additionally, the concentration of protons ($H^+$) affects the stability of the product. The invention recognizes that the proton concentration can be controlled by using an acid that has a lesser ability at a given pH to donate a proton (i.e., the acid can provide buffering capacity). For example, conducting the process with acetic acid instead of hydrochloric acid is optimal when the desired pH of the final solution is approximately the pKa of acetic acid. This can be achieved by mixing ratios in water of 250× or greater, meaning 1 part proton donor at 100% concentration (e.g., HCl or acetic acid) to 250 parts water.

The invention generally relates to methods of producing hypochlorous acid (HOCl). In certain embodiments, methods of the invention involve mixing together in water in an air-free environment, a compound that generates a proton (H$^+$) in water and a compound that generates a hypochlorite anion (OCl$^-$) in water to thereby produce air-free hypochlorous acid. The water may be tap water or purified water, such as water purchased from a water purification company, such as Millipore (Billerica, Mass.). Generally, the pH of the water is maintained from about 4.5 to about 9 during the method, however the pH may go above and below this range during the production process. Conducting methods of the invention in an air-free environment prevents the build-up of chlorine gases during the production process. Further, conducting methods of the invention in an air-free environment further stabilizes the produced HOCl.

Any compound that produces a hypochlorite anion (OCl$^-$) in water may be used with methods of the invention. Exemplary compounds include NaOCl and Ca(OCl)$_2$. In particular embodiments, the compound is NaOCl. Any compound that produces a proton (H$^+$) in water may be used with methods of the invention. Exemplary compounds are acids, such as acetic acid, HCl and H$_2$SO$_4$. In particular embodiments, the compound is HCl. In preferred embodiments, the compound is acetic acid because it is a weaker acid with a preferred pKa to HCl, meaning, it donates less protons during the reaction than HCl and able to maintain the preferred pH level better.

Methods of the invention can be conducted in any type of vessel or chamber or fluidic system. In certain embodiments, a fluidic system 100 as shown in FIG. 1 is used to perform methods of the invention. The system 100 includes a series of interconnected pipes 101a-c with a plurality of mixing devices 102 and 103 in-line with the plurality of pipes 101a-c. The pipes and the mixing devices can be interconnected using seals such that all air can be purged from the system, allowing for methods of the invention to be performed in an air-free environment. In certain embodiments, methods of the invention are also conducted under pressure. Conducting methods of the invention in an air-free environment and under pressure allows for the production of HOCl that does not interact with gases in the air (e.g., oxygen) that may destabilize the produced HOCl.

Pipes 101a-c generally have an inner diameter that ranges from about 5 mm to about 50 mm, more preferably from about 17 mm to about 21 mm. In specific embodiments, the pipes 101a-c have an inner diameter of about 21 mm. Pipes 101a-c generally have a length from about 10 cm to about 400 cm, more preferably from about 15 cm to about 350 cm. In certain embodiments, pipes 101a-c have the same length. In other embodiments, pipes 101a-c have different lengths. In specific embodiments, pipe 101a has a length of about 105 cm, pipe 101b has a length of about 40 cm, and pipe 101c has a length of about 200 cm.

The pipes and mixers can be made from any inert material such that material from the pipes and mixers does not become involved with the reaction occurring within the fluidic system. Exemplary materials include PVC-U. Pipes are commercially available from Georg Ficher AB. The pipes and mixers can be configured to have a linear arrangement such that the pipes and the mixers are arranged in a straight line. Alternatively, the pipes and mixers can have a non-linear arrangement, such that the water must flow through bends and curves throughout the process. System 100 shows a non-linear configuration of the pipes 101a-c and mixers 102 and 103.

Pipe 101a is an inlet pipe that receives the water that will flow through the system. Generally, the water in pipes 101a-c is under a pressure of at least about 0.1 bar, such as for example, 0.2 bar or greater, 0.3 bar or greater, 0.4 bar or greater, 0.5 bar or greater, 0.7 bar or greater, 0.9 bar or greater, 1.0 bar or greater, 1.2 bar or greater, 1.3 bar or greater, or 1.5 bar or greater. At such pressures, a turbulent water flow is produced, thus the reagents are introduced to a highly turbulent water flow which facilitates an initial mixing of the reagents with the water prior to further mixing in the mixing devices 102 and 103.

In order to control the pH during the production process, the incoming water should have a buffering capacity in the range of pH 3.5-9.0, more preferably from 6.0 and 8.0, to facilitate addition of the compounds that generates the proton and the compound that generates the hypochlorite anion. The dissolved salts and other molecules found in most tap waters gives the tap water a buffering capacity in the range of pH 5.5-9.0, and thus tap water is a suitable water to be used with methods of the invention.

In certain embodiments, deionized water with the addition of known buffering agents to produce a water having a buffering capacity in the range of pH 3.5-9.0 is used. On example of a buffer in this particular range is phosphate buffer. For greater process control and consistency, using a formulated deionized water may be preferable to using tap water because tap water can change between locations and also over time. Additionally, using deionized water with known additives also ensures a stable pH of the incoming water flow. This process is discussed in greater detail below.

In particular embodiments, an initial pH of the water prior to addition of either the compounds that generates the proton or the compound that generates the hypochlorite anion is at least about 8.0, including 8.1 or greater, 8.2 or greater, 8.3 or greater, 8.4 or greater, 8.5 or greater, 8.6 or greater, 8.7 or greater, 8.8 or greater, 8.9 or greater, 9.0 or greater, 9.5 or greater, 10.0 or greater, 10.5 or greater, or 10.8 or greater. In specific embodiments, the pH of the water prior to addition of either the compound that generates the proton or the compound that generates the hypochlorite anion is 8.4.

Methods of the invention include introducing to the water the compound that generates the proton and the compound that generates the hypochlorite anion in any order (e.g., simultaneously or sequentially) and in any manner (aqueous form, solid form, etc.). For example, the compound that generates the proton and the compound that generates the hypochlorite anion are each aqueous solutions and are introduced to the water sequentially, e.g., the compound that generates the proton may be introduced to the water first and the compound that generates the hypochlorite anion may be introduced to the water second. However, methods of the invention include other orders for sequential introduction of the compound that generates the proton and the compound that generates the hypochlorite anion.

System 100 is configured for sequential introduction of reagents to the water flow, and the process is described herein in which the compound that generates the proton is introduced to the water first and the compound that generates the hypochlorite anion is introduced to the water second. In certain embodiments, the compound that generates the proton and the compound that generates the hypochlorite anion are introduced to the water in small aliquots, e.g, from about 0.1 mL to about 0.6 mL. The iterative and minute titrations make it possible to control the pH in spite of additions of acid (compound that generates the proton) and alkali (the compound that generates the hypochlorite anion). In certain embodiments, no more than about 0.6 mL amount of compound that generates the proton is introduced to the water at a single point in time. In other embodiments, no more than about 0.6 mL amount of the compound that generates the hypochlorite anion is introduced to the water at a single point in time.

To introduce the reagents to the water, pipe 101a includes an injection port 104 and pipe 101b includes an injection port 105. The injection ports 104 and 105 allow for the introduction of reagents to the water flow. In this embodiments, aqueous compound that generates the proton is introduced to the water in pipe 101a via injection port 104. The compound that generates the proton is introduced by an infusion pump that is sealably connected to port 104. In this manner, the flow rate, and thus the amount, of compound that generates the proton introduced to the water at any given time is controlled. The infusion pump can be controlled automatically or manually. The rate of introduction of the compound that generates the proton to the water is based upon the incoming water quality (conductivity and pH level) and the pressure and the flow of the incoming water. In certain embodiments, the pump is configured to introduce about 6.5 liters per hour of hydrochloric acid into the water. The introducing can be a continuous infusion or in an intermittent manner. Since the water is flowing though the pipes in a turbulent manner, there is an initial mixing of the compound that generates the proton with the water upon introduction of the hydrochloric acid to the water.

Figure 2:
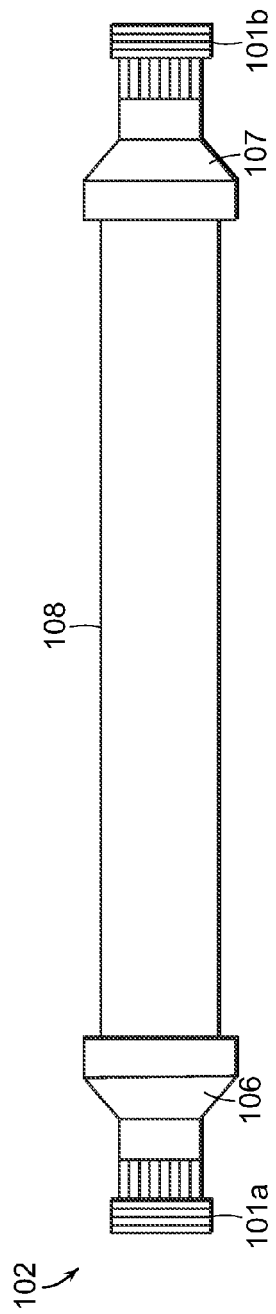
FIG. 2 is a schematic showing a magnified view of the mixing device shown in FIG. 1.

Further mixing occurs when the water enters the first mixing device 102. FIG. 2 shows a magnified view of the mixing device 102 shown in FIG. 1. In the illustrated embodiment, the mixing device includes a length of about 5.5 cm and a diameter of about 5 cm. One of skill in the art will recognize that these are exemplary dimensions and methods of the invention can be conducted with mixing devices having different dimensions than the exemplified dimensions. Mixing device 102 includes a fluidic inlet 106 that sealably couples to pipe 101a and a fluidic outlet 107 that sealably couples to pipe 101b. In this manner, water can enter the mixing chamber 108 of device 102 from pipe 101a and exit the chamber 108 of device 102 through pipe 101b.

Figure 3:
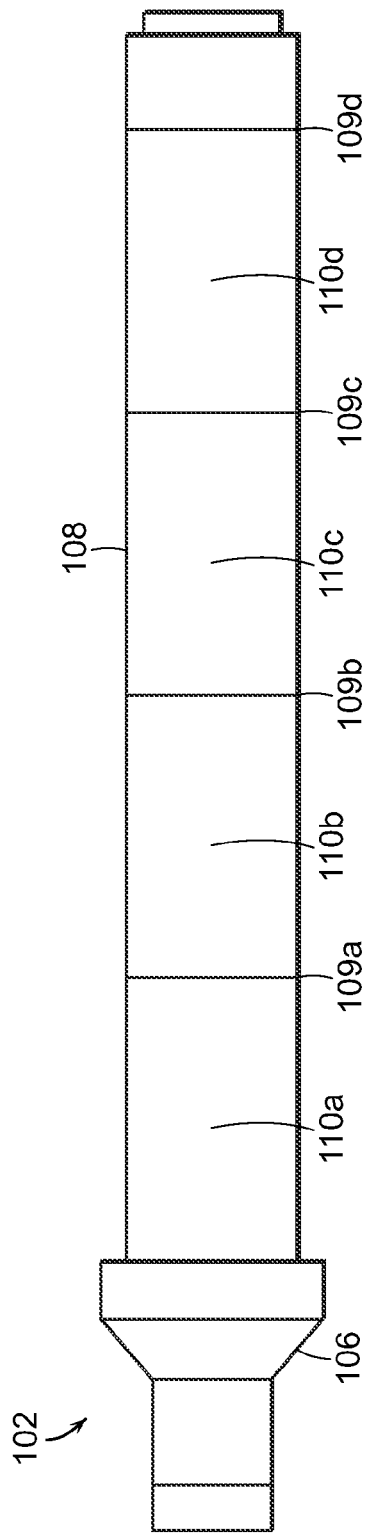
FIG. 3 is a schematic showing an internal view of the mixing chamber of the mixing device.
Figure 4:
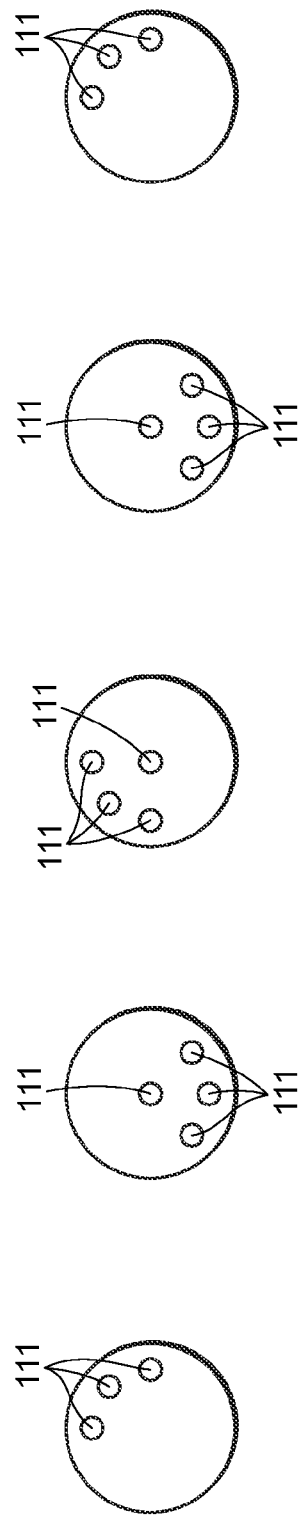
FIG. 4 is a schematic showing a front view of the members that divide the mixing chamber into a plurality of sub-chambers. This view shows the apertures in the members.

The mixing device 102 is configured to produce a plurality of fluidic vortexes within the device. An exemplary device configured in such a manner is shown in FIG. 3, which is a figure providing an internal view of the chamber 108 of device 102. The chamber 108 includes a plurality of members 109, the members being spaced apart and fixed within the chamber 108 perpendicular to the inlet and the outlet in order to form a plurality of sub-chambers 110. Each member 109 includes at least one aperture 111 that allows fluid to flow there through. FIG. 4 shows a front view of the members 109 so that apertures 111 can be seen. The size of the apertures will depend on the flow of water and the pressure in the system.

Any number of members 109 may be fixed in the chamber 108, the number of members 109 fixed in the chamber 108 will depend on the amount of mixing desired. FIG. 4 shows four members 109a-d that are fixed in the chamber to produce four sub-chambers 110a-d. The members 109 may be spaced apart a uniform distance within the chamber 108, producing sub-chambers 110 of uniform size. Alternatively, the members 109 may be spaced apart at different distances within the chamber 108, producing sub-chambers 110 of different size. The members 109 are of a size such that they may be fixed to an interior wall within the chamber 108. In this manner, water cannot flow around the members and can only pass through the apertures 111 in each member 109 to move through mixing device 102. Generally, the members will have a diameter from about 1 cm to about 10 cm. In specific embodiments, the members have a diameter of about 3.5 cm.

A fluidic vortex is produced within each sub-chamber 110a-d. The vortices result from flow of the water through the apertures 111 in each member 109. Methods of the invention allow for any arrangement of the apertures 111 about each member 109. FIG. 4 illustrates non-limiting examples of different arrangements of the apertures 111 within a member 109. The apertures may be of any shape. FIG. 4 illustrates circular apertures 111. In certain embodiments, all of the apertures 111 are located within the same place of the members 109. In other embodiments, the apertures 111 are located within different places of the members 109. Within a single member 109, all of the apertures 111 may have the same diameter. Alternatively, within a single member 110, at least two of the apertures 111 have different sizes. In other embodiments, all of the apertures 111 within a single member 110 have different sizes.

In certain embodiments, apertures 111 in a member 110 have a first size and apertures 111 in a different member 110 have a different second size. In other embodiments, apertures 111 in at least two different members 110 have the same size. The size of the apertures will depend on the flow of water and the pressure in the system. Exemplary aperture diameters are from about 1 mm to about 1 cm. In specific embodiments, the apertures have a diameter of about 6 mm.

The solution enters mixing device 102 through inlet 106, which is sealably mated with pipe 101a. The solution enters the chamber 108 and turbulent mixing occurs in each of sub-chambers 110a-d as the solution pass through members 109a-d via the apertures 111 in each member 109a-d. After mixing in the final sub-chamber 110d, the water exits the chamber 108 via the fluidic outlet 107 which is sealably mated to pipe 101b.

The compound that generates the hypochlorite anion is next introduced to the solution that is flowing through pipe 101b via injection port 105. The compound that generates the hypochlorite anion is introduced by an infusion pump that is sealably connected to port 105. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and the flow of the solution. In certain embodiments, the pump is configured to introduce about 6.5 liters per hour of compound that generates the hypochlorite anion into the solution. The introducing can be a continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 103. Mixing device 103 includes all of the features discussed above with respect to mixing device 102. Mixing device 103 may be configured the same or differently than mixing device 102, e.g., same or different number of sub-chambers, same or different diameter of apertures, same or different sizes of sub-chambers, etc. However, like mixing device 102, mixing device 103 is configured to produce a fluidic vortex within each sub-chamber.

The solution enters mixing device 103 through an inlet in the device, which is sealably mated with pipe 101b. The solution enters the mixing chamber and turbulent mixing occurs in each sub-chamber of the mixing device as the solution pass through members in the chamber via the apertures in each member. After mixing in the final sub-chamber, the water exits the chamber via the fluidic outlet in the mixing device which is sealably mated to pipe 101c.

Figure 8:
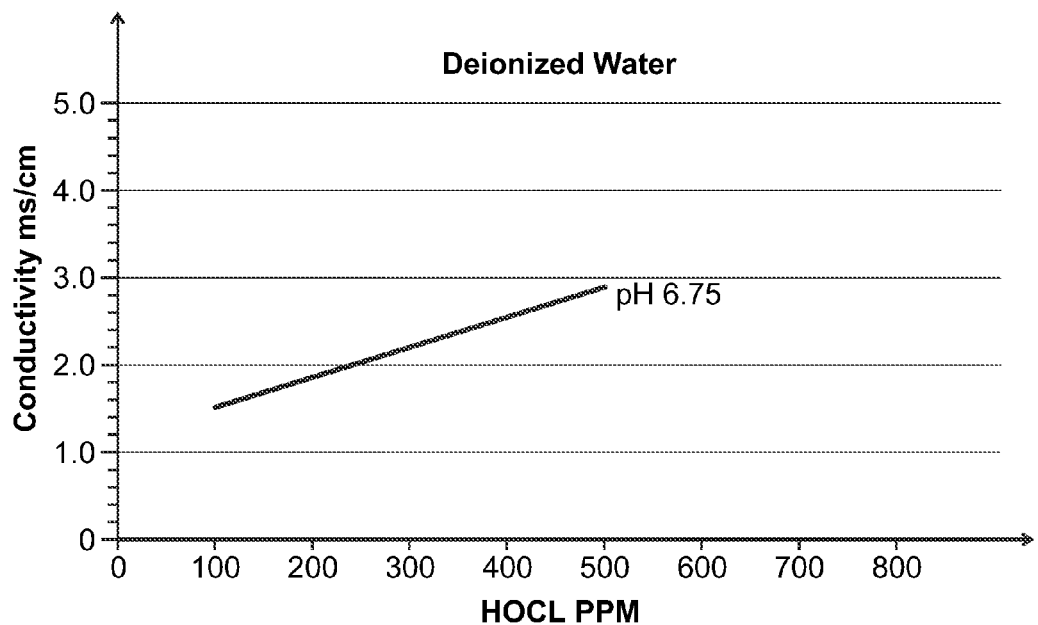
FIG. 8 is a graph of a calibration curve showing HOCl concentration (ppm) calculated indirectly versus conductivity.

At this point, the reaction has been completed and the HOCl has been formed. The production is controlled in-line by measuring pH and conductivity. The pH is used in combination with conductivity based on a pre-calibrated relation between the conductivity and concentration of HOCl measured with spectrophotometry. The measured conductivity is a measure of the solvent's ability to conduct an electric current. Comparing the same matrix with different known concentrations of HOCl and OCl—, a calibration curve (FIG. 8) has been established that is used in combination with the pH meter to regulate the titrations and control the process.

Figure 5:
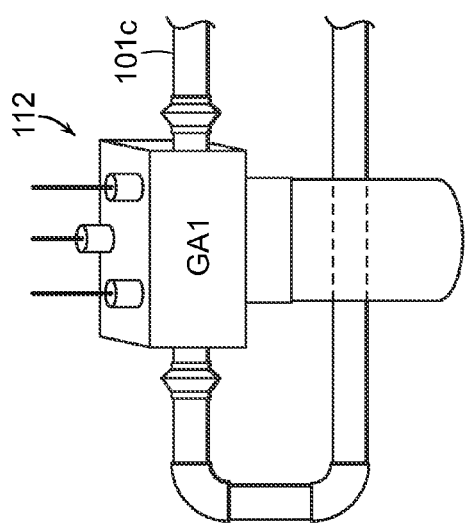
FIG. 5 is a schematic showing a valve configured with measuring sensors for switching from a waste line to a product collection line.
Figure 6:
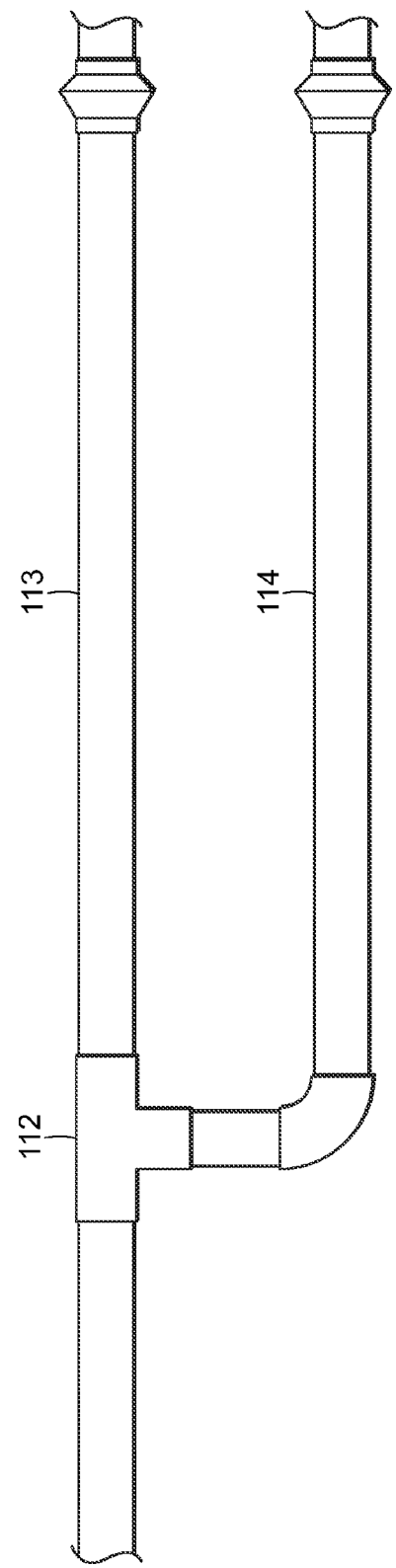
FIG. 6 is a schematic showing the valve in-line with the waste line and the product collection line.

Pipe 101c can be connected to a switch valve 112 that switches between a waste line 113 and a product collection line 114. Shown in FIGS. 5 and 6. The valve 112 includes the pH meter and the conductivity measuring device. These devices measure the concentration (ppm), purity, and pH of the HOCl being produced and provide feedback for altering such properties of the produced HOCl. Once the HOCl being produced in pipe 101c meets the required concentration, purity, and pH, the valve 112 switches from the waste line 113 to the product collection line 114 to collect the desired product.

The HOCl that has been produced in an air-free manner is collected and bottled in an air-free manner. Placing liquids into a bottle in an air-free manner is known in the art. An exemplary method includes placing an inflatable vessel (such as a balloon) into a bottle. The inflatable vessel is connected directly to the collection line 114 and the HOCl is pumped directed into the inflatable vessel in the bottle without ever being exposed to air. Another method involves filling the bottles under vacuum. Another air-free filling method involves filling the bottles in an environment of an inert gas that does not interact with the HOCl, such as an argon environment.

The produced hypochlorous acid is air-free and will have a pH from about 4.5 to about 7.5. However, the pH of the produced HOCl can be adjusted post production process by adding either acid (e.g., HCl) or alkali (e.g., NaOCl) to the produced hypochlorous acid. For example, a pH of between about 4.5 and about 7 is particularly suitable for the application of reprocessing heat sensitive medical instruments. Other applications, such as its use in non-medical environments, for example as in the processing of poultry and fish and general agricultural and petrochemical uses, the breaking down of bacterial biofilm and water treatment, may demand different pH levels.

The process can be performed manually or in an automated manner. Fluidic systems described herein can be operably connected to a computer that controls the production process. The computer may be a PCL-logic controller system. The computer opens and closes the valves for the water inlet, the waste water outlet, and the product outlet according to the feedback received from the sensors in the system (e.g., conductivity, pH, and concentration of product (ppm) being produced). The computer can also store the values for the water pressures and water amounts and can adjust these according to the feedback received from the sensors regarding the properties of the HOCl being produced. The computer can also control the infusion pumps that inject the reagents into the water for the production process.

The process can be performed iteratively in that pipe 101c can be attached to a second fluidic system and the produced HOCl is then flowed through the second system where the process described above is repeated with the starting solution being HOCl instead of water. In this manner, an increased yield of HOCl is produced. Any number of fluidic systems may be interconnected with methods of the invention.

Figure 7:
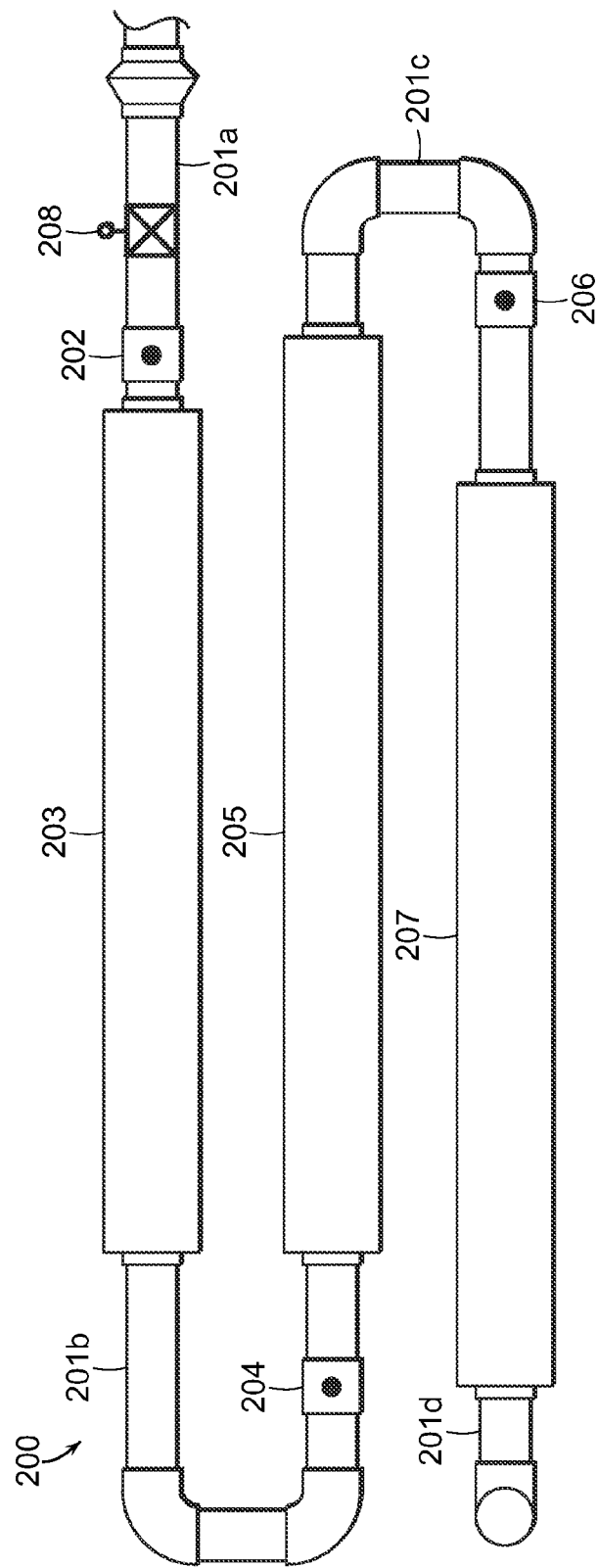
FIG. 7 is a schematic showing another exemplary system for producing hypochlorous acid according to methods of the invention. This system is configured for automated use with buffered deionized water. The buffer can either be included in the inflowing water or can be introduced through an injection port. The buffer may also be mixed during the mixing process by using NaOH in NaOCl or separately injected and acetic acid or others similar acids or bases.

FIG. 7 is a schematic showing another exemplary system 200 for producing hypochlorous acid according to methods of the invention. System 200 is configured for regulation of the pH of the incoming water and injecting buffer for stability. In system 200, water is introduced into pipe 201a. Pipe 201a has a pH meter 208 connected to it. pH meter 208 measures the pH of the incoming water. The pH meter 208 is connected to injection port 202. The injection port 202 allows for the introduction of at least one buffering agent to the incoming water. The buffering agent is introduced by an infusion pump that is sealably connected to port 202. In this manner, the flow rate, and thus the amount, of buffering agent introduced to the water at any given time is controlled. The infusion pump can be controlled automatically or manually. The rate of introduction of the buffering agent to the water is based upon the incoming water quality (conductivity and pH level), the buffer composition, and the pressure and the flow of the incoming water. The introducing can be a continuous infusion or in an intermittent manner. Since the water is flowing through the pipe 201a in a turbulent manner, there is an initial mixing of the buffering agent with the water upon introduction of the buffering to the water. This initial mixing may be sufficient to properly adjust the properties of the incoming water.

In certain embodiments, further mixing of the water and buffer is performed prior to conducting the process of producing the HOCl. In those embodiments, further mixing occurs when the water with buffering agent enters the first mixing device 203. Mixing device 203 includes all of the features discussed above with respect to mixing device 102. Mixing device 203 may be configured the same or differently than mixing device 102, e.g., same or different number of sub-chambers, same or different diameter of apertures, same or different sizes of sub-chambers, etc. However, like mixing device 102, mixing device 203 is configured to produce a fluidic vortex within each sub-chamber.

The solution enters mixing device 203 through an inlet in the device, which is sealably mated with pipe 201a. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 202b. The water has a pH of at least about 8.0, preferably 8.4, and a buffering capacity of pH 5.5-9.0.

The process is now conducted as described above for producing HOCl. The compound that generates the proton is next introduced to the water that is flowing through pipe 201b via injection port 204. The compound that generates the proton is introduced by an infusion pump that is sealably connected to port 204. In this manner, the flow rate, and thus the amount, of compound that generates the proton introduced to the water at any given time is controlled. The infusion pump can be controlled automatically or manually. The rate of introduction of the compound that generates the proton to the water is based upon properties of the water (conductivity and pH level), the buffer composition, and the pressure and the flow of the water. In certain embodiments, the pump is configured to introduce from about 6.5 liters per hour to about 12 liters per hour of compound that generates the proton into the water. The introducing can be a continuous infusion or in an intermittent manner. Since the water is flowing though the pipes in a turbulent manner, there is an initial mixing of the compound that generates the proton with the water upon introduction of the hydrochloric acid to the water.

Further mixing occurs when the solution enters the second mixing device 205. Mixing device 205 includes all of the features discussed above with respect to mixing device 102. Mixing device 205 may be configured the same or differently than mixing device 203, e.g., same or different number of sub-chambers, same or different diameter of apertures, same or different sizes of sub-chambers, etc. However, like mixing device 203, mixing device 205 is configured to produce a fluidic vortex within each sub-chamber.

The solution enters mixing device 205 through an inlet in the device, which is sealably mated with pipe 201*b*. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 201*c*.

The compound that generates the hypochlorite anion is next introduced to the solution that is flowing through pipe 201*c* via injection port 206. The compound that generates the hypochlorite anion is introduced by an infusion pump that is sealably connected to port 206. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and the flow of the solution. In certain embodiments, the pump is configured to introduce about 6.5-12 liters per hour of compound that generates the hypochlorite anion into the solution. The amount introduced depends on the desired concentration of HOCl (ppm) and flow of water through the pipes. The introducing can be a continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 207. Mixing device 207 includes all of the features discussed above with respect to mixing device 102. Mixing device 207 may be configured the same or differently than mixing devices 205 or 203, e.g., same or different number of sub-chambers, same or different diameter of apertures, same or different sizes of sub-chambers, etc. However, like mixing devices 205 and 203, mixing device 207 is configured to produce a fluidic vortex within each sub-chamber.

The solution enters mixing device 207 through an inlet in the device, which is sealably mated with pipe 201*c*. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 201*d*.

At this point, the reaction has been completed and the HOCl has been formed. The produced HOCl can be measured and collected as described above. Pipe 201*d* can be connected to a switch valve that switches between a waste line and a product collection line. The valve includes a pH meter and a conductivity measuring device. These devices measure the concentration, purity, and pH of the HOCl being produced and provide feedback for altering such properties of the produced HOCl. Once the HOCl being produced in pipe 201*d* meets the required concentration, purity, and pH, the valve switches from the waste line to the product collection line to collect the desired product.

In another embodiment, a deionizer is placed in-line with incoming water. The deionizer deionizes the water and then a buffering agent is added to the deionized water. The production process is then conducted as described for embodiments of system 200 to produce water having a pH of at least about 8, for example 8.4, and a buffering capacity of pH 6-8.

The HOCl produced by the above process can be used in numerous different applications, for example medical, foodservice, food retail, agricultural, wound care, laboratory, hospitality, dental, delignification, or floral industries.

INCORPORATION BY REFERENCE

Any and all references and citations to other documents, such as patents, patent applications, patent publications, journals, books, papers, web contents, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Product Analysis

Figure 9:
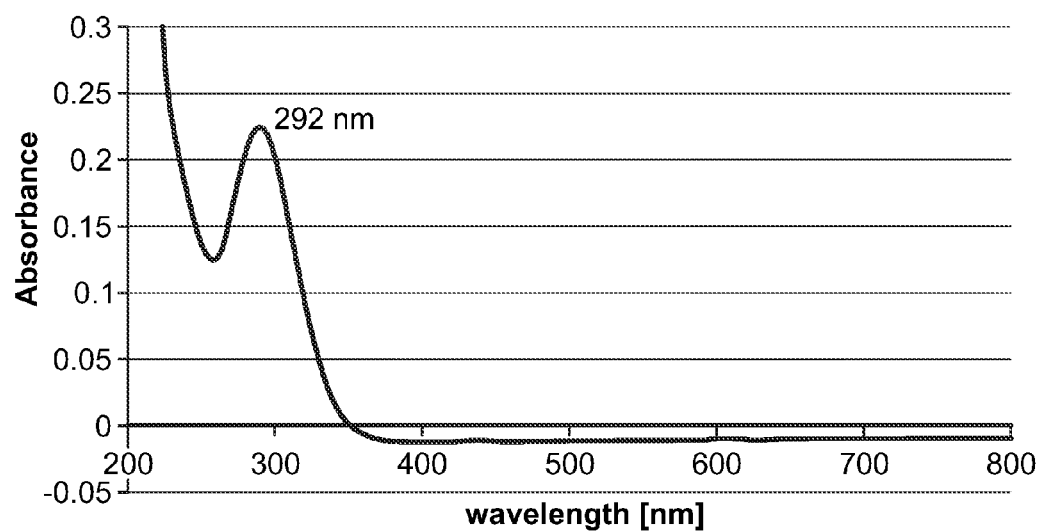
FIG. 9 is a graph showing a spectrophotometric analysis of the produced HOCl. The gases generally produced during production of HOCl are $ClO_2$, $Cl_2O$ and $Cl_2$, all of which are detectable in the visible range as yellow or yellow-red. The graph shows no absorption from colored gases in the produced HOCl.

When spectrophotometry is expanded to also cover the visible range it is possible to detect colors. The gases generally produced during production of HOCl are $ClO_2$, $Cl_2O$ and $Cl_2$, all of which are detectable in the visible range as yellow or yellow-red. Tzanavaras et al. (Central European J. of Chemistry, 2007, 5(1)1-12). Data in FIG. 9 illustrates that the HOCl produced by methods on the invention shows no absorption from colored gases as shown by the lack of colored substance. It is known that HOCl produces a peak at 292 nm (Feng et al. 2007, J. Environ. Eng. Sci. 6, 277-284).

Example 2

HOCl produced by the process described above was stored under heat stress at 40° C. in order to accelerate degradation using four different types of aqueous solutions: (1) reagent grade water (deionized water); (2) tap water; (3) reagent grade water with a phosphate buffer; and (4) tap water with a phosphate buffer. Characteristics of the HOCl product were monitored after the initial reaction (T=0); four weeks (T=4); eight weeks (T=8); and twelve weeks (T=12).

Figure 10:
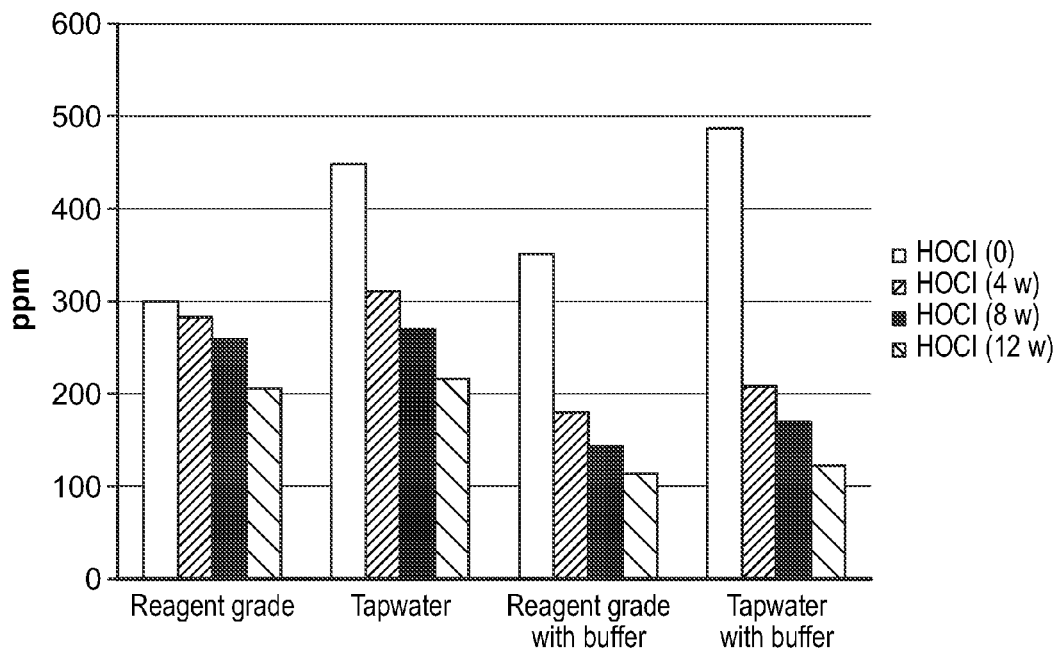
FIG. 10 is a graph showing the amount (parts per million (ppm)) of HOCl initially produced (T=0) and its stability over time.

FIG. 10 is a graph showing the amount (parts per million (ppm)) of HOCl initially produced (T=0) and its stability over time. The data show that the reagent grade water (deionized water) without phosphate buffer is the most stable over the twelve weeks, showing the least amount of product degradation from the initial amount produced. The deionized water produces a much more stable product than that produced using tap water. Additionally, and surprisingly, the data show that phosphate buffer may negatively impact amount of HOCl product produced.

Figure 11:
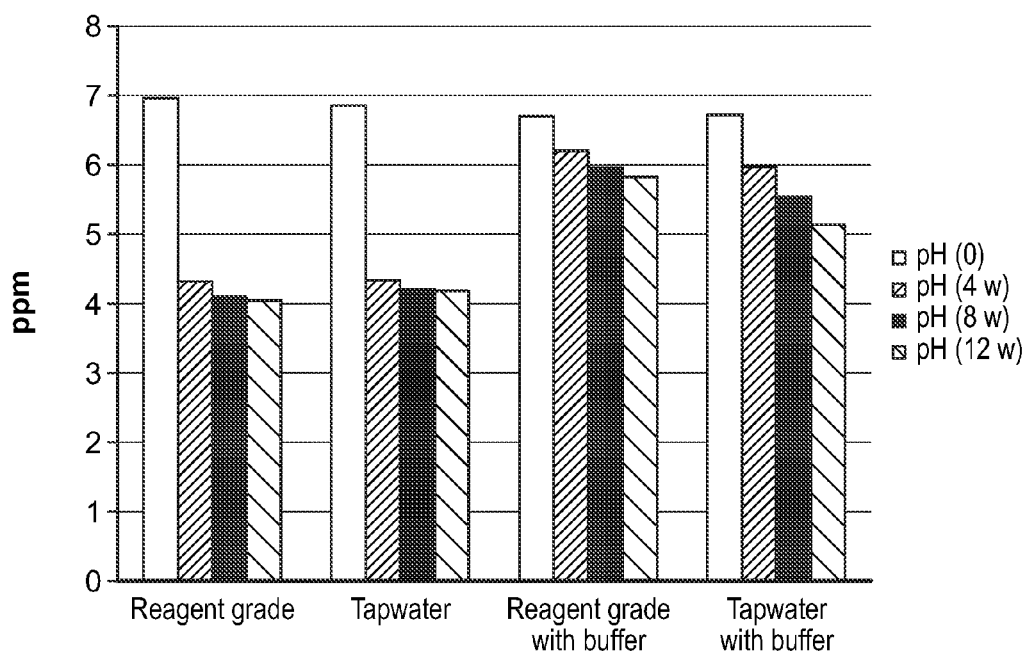
FIG. 11 is a graph showing how the pH of the HOCl product changed over time.

FIG. 11 is a graph showing how the pH of the HOCl product changed over time. In all cases, the pH decreased over time, however, for all cases, the pH stayed in the range of pH=4 to pH=7 over the twelve weeks.

Figure 12:
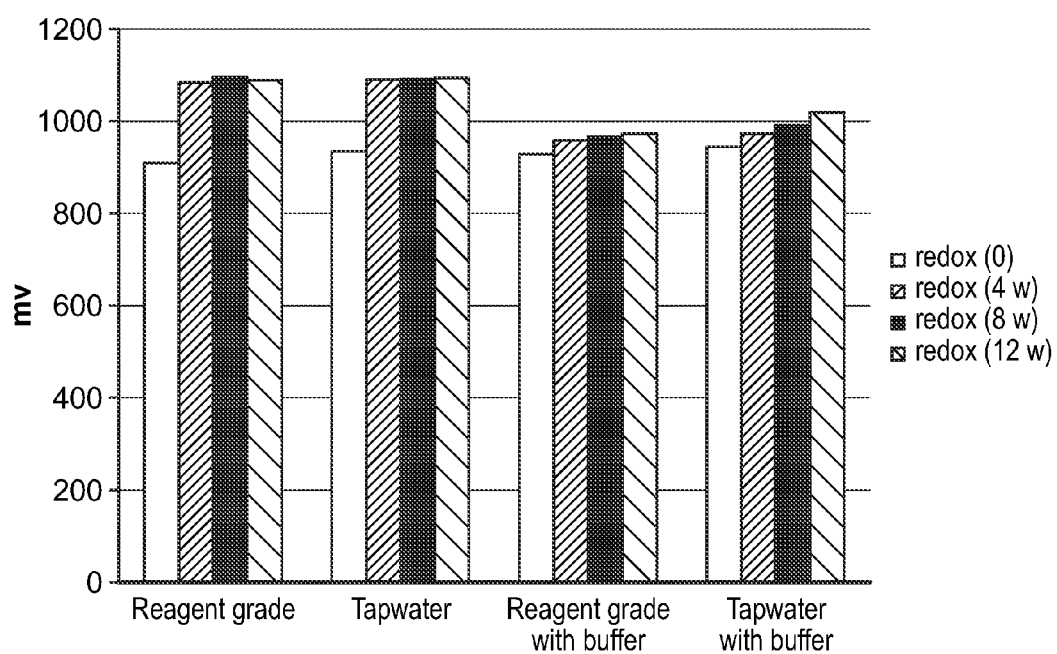
FIG. 12 is a graph showing the oxidation and reduction (redox) of the HOCl product over time.

FIG. 12 is a graph showing the oxidation capacity of the HOCl product over time. The data show that the product retained oxidation capacity over the twelve weeks regardless of the starting water.

Example 3

Acetic Acid Compared to Hydrochloric Acid

Using the above described process, HOCl was produced using hydrochloric acid (HCl) and acetic acid and thereafter stored under heat stress at 40C. The amount of HOCl initially produced was recorded (T=0) and then the amount of HOCl product remaining after twelve days was recorded. Three batches of each were produced. The data for the HCl produced HOCl is shown in Table 1. The data for the acetic acid produced HOCl is shown in Table 2.

TABLE 1

HOCl produced with HCl

| Batch number | Initial amount (ppm) | Initial pH | Amount after 12 days (ppm) | pH after 12 days | Amount of degradation | Amount pH change |
|---|---|---|---|---|---|---|
| 1 | 192 | 7.12 | 159 | 5.71 | 17.2% | 19.8% |
| 2 | 183 | 5.88 | 147 | 4.01 | 19.7% | 31.8% |
| 3 | 189 | 5.21 | 154 | 3.97 | 18.5% | 23.8% |

TABLE 2

HOCl produced with acetic acid

| Batch number | Initial amount (ppm) | Initial pH | Amount after 12 days (ppm) | pH after 12 days | Amount of degradation | Amount pH change |
|---|---|---|---|---|---|---|
| 1 | 205 | 4.62 | 180 | 4.50 | 12.4% | 2.7% |
| 2 | 205 | 5.33 | 178 | 5.04 | 13.3% | 5.4% |
| 3 | 207 | 4.07 | 178 | 3.89 | 13.9% | 4.6% |

The data show that using acetic acid provides greater product stability, most likely due to greater stability in the pH. Without being limited by any particular theory or mechanism of action, it is believed that the different protonation capacity of acetic acid as compared to hydrochloric acid, i.e., acetic acid donates fewer protons to a liquid than hydrochloric acid, results in greater HOCl stability over time.

What is claimed is:

1. A method of producing hypochlorous acid (HOCl), the method comprising the steps of: mixing together in water in a chamber from which air has been purged, a compound that generates a proton ($H^+$) in water and a compound that generates a hypochlorite anion ($OCl^-$) in water, thereby to produce air-free hypochlorous acid wherein the compound that generates the proton is selected from the group consisting of acetic acid and HCl.

2. The method according to claim 1, wherein the hypochlorous acid comprises a pH from about 4.5 to about 7.5.

3. The method according to claim 1, wherein the compound that generates the proton and the compound that generates the hypochlorite anion are introduced to the water sequentially.

4. The method according to claim 3, wherein the compound that generates the proton is introduced to the water first and the compound that generates the hypochlorite anion is introduced to the water second.

5. The method according to claim 3, wherein the compound that generates the hypochlorite anion proton is introduced to the water first and the compound that generates the proton is introduced to the water second.

6. The method according to claim 4, wherein an initial pH of the water is increased prior to addition of the compound that generates the proton.

7. The method according to claim 6, wherein the mixing is turbulent mixing.

8. The method according to claim 7, wherein the compound that generates the proton is introduced to the water and turbulently mixed with the water prior to the introduction to the water of the compound that generates the hypochlorite anion.

9. The method according to claim 8, wherein the compound that generates the hypochlorite anion is introduced to the water after the compound that generates the proton has been turbulently mixed with the water, and after introduction, the compound that generates the hypochlorite anion is turbulently mixed with the water.

10. The method according to claim 1, wherein the compound that generates the hypochlorite anion is selected from the group consisting of sodium hypochlorite (NaOCl), $Mg(OCl)_2$ and $Ca(OCl)_2$.

11. The method according to claim 1, wherein the water has a buffering capacity from about pH 3.5 to about pH 9.0.

12. The method according to claim 11, wherein the water is tap water.

13. The method according to claim 11, wherein the water is purified water to which at least one buffering agent has been added.

14. The method according to claim 11, wherein the buffering agent selected from the group consisting of acetic buffer and phosphate buffer.

15. The method according to claim 1, wherein the water is flowing through a pipe.

16. The method according to claim 15, wherein the water has a pressure of at least about 0.5 bar.

17. The method according to claim 1, wherein no more than about 0.6 mL amount of compound that generates the proton is introduced to the water at a single point in time.

18. The method according to claim 1, wherein no more than about 0.6 mL amount of the compound that generates the hypochlorite anion ($OCl^-$) is introduced to the water at a single point in time.

19. The method according to claim 1, wherein the method is performed without use of chlorine gas or use of electrolysis.

20. The method according to claim 1, wherein a plurality of mixes are iteratively performed.

21. A method of producing hypochlorous acid (HOCl), the method comprising:
- introducing hydrochloric acid (HCl) to a flow of water;
- turbulently mixing the HCl with the flowing water in a first mixing device from which air has been purged;
- introducing sodium hypochlorite (NaOCl) to the water after the water has exited the first mixing device; and
- turbulently mixing the NaOCl with the flowing water in a second mixing device from which air has been purged, thereby producing hypochlorous acid (HOCl), wherein the method is performed in an air-free environment and under pressure.

* * * * *

UNITED STATES PATENT AND TRADEMARK OFFICE
CERTIFICATE OF CORRECTION

| | | |
|---|---|---|
| PATENT NO. | : 9,492,479 B2 | |
| APPLICATION NO. | : 13/770738 | |
| DATED | : November 15, 2016 | |
| INVENTOR(S) | : Almås et al. | |

It is certified that error appears in the above-identified patent and that said Letters Patent is hereby corrected as shown below:

In the Claims

In Column 14, Lines 18-21, Claim 5 currently reads:

-- 5. The method according to claim 3, wherein the compound that generates the hypochlorite anion proton is introduced to the water first and the compound that generates the proton is introduced to the water second. --

Should read:

-- 5. The method according to claim 3, wherein the compound that generates the hypochlorite anion is introduced to the water first and the compound that generates the proton is introduced to the water second. --

Signed and Sealed this
Tenth Day of January, 2017

Michelle K. Lee
*Director of the United States Patent and Trademark Office*